United States Patent [19]

Kusuda et al.

[11] Patent Number: 5,449,829
[45] Date of Patent: Sep. 12, 1995

[54] PROCESS FOR THE PREPARATION OF DIPHENYLAMINE

[75] Inventors: Chiyuki Kusuda, Kumamoto; Masaru Wada; Teruyuki Nagata, both of Ohmuta, all of Japan

[73] Assignee: Mitsuit Toatsu Chemicals, Inc., Tokyo, Japan

[21] Appl. No.: 260,903

[22] Filed: Jun. 15, 1994

[30] Foreign Application Priority Data

Jun. 22, 1993 [JP] Japan .................................. 5-150287
Jun. 22, 1993 [JP] Japan .................................. 5-150288

[51] Int. Cl.⁶ .......................................... C07C 209/04
[52] U.S. Cl. ..................... 564/397; 564/307; 564/402; 564/433
[58] Field of Search ................. 564/307, 397, 402, 433

[56] References Cited

U.S. PATENT DOCUMENTS

| | | | |
|---|---|---|---|
| 3,219,702 | 11/1965 | Van Verth et al. | 260/571 |
| 3,219,704 | 11/1965 | Wilder et al. | 260/571 |
| 3,553,268 | 1/1971 | Solomon et al. | 260/581 |
| 3,931,298 | 1/1976 | Wollensak | 564/402 |
| 4,804,783 | 2/1989 | Nagata et al. | 564/402 |
| 4,952,731 | 8/1990 | Nagata et al. | 564/402 |
| 5,196,592 | 3/1993 | Immel et al. | 564/415 |
| 5,344,987 | 9/1994 | Immel et al. | 564/397 |

FOREIGN PATENT DOCUMENTS 2-188555 7/1990 Japan .

*Primary Examiner*—Richard L. Raymond
*Attorney, Agent, or Firm*—Burns, Doane, Swecker & Mathis

[57] ABSTRACT

A diphenylamine with both the phenyl groups being substituted is prepared by reacting a phenol with ammonia in the presence of a hydrogen transfer catalyst and a cyclohexanone; or by converting a portion of the phenol to the cyclohexanone in the presence of a hydrogen transfer catalyst and under hydrogen pressure and then reacting the remaining portion of the phenol with ammonia in the presence of the cyclohexanone so converted and the hydrogen transfer catalyst. The diphenylamine can be obtained very efficiently.

8 Claims, No Drawings

PROCESS FOR THE PREPARATION OF DIPHENYLAMINE

BACKGROUND OF THE INVENTION

1. Field of the Invention

This invention relates to a process for the preparation of a novel diphenylamine in which each phenyl group is substituted. Diphenylamines available according to the present invention are useful as antioxidants for mineral oils, synthetic oils and the like and also as resin additives.

2. Description of the Related Art

As a process for the preparation of a diphenylamine containing one or more substituents on each phenyl group, it has already been known to prepare dinonyldiphenylamine by subjecting nonene and diphenylamine to Friedel-Crafts alkylation in the presence of a metal halide such as aluminum chloride or zinc chloride or an acid catalyst such as sulfuric acid, phosphoric acid or acid clay (Japanese Patent Laid-Open No. 188555/1990).

This process, however, is accompanied with the drawback that it is difficult to add a sufficient amount of nonene to diphenylamine. Thus, the resultant dinonyldiphenylamine contains the mono-substituted derivative and is low in purity.

SUMMARY OF THE INVENTION

The present inventors have conducted extensive research with a view toward overcoming the above drawback and developing an industrially more advantageous process. As a result, it has been found that a diphenylamine with both the phenyl groups being substituted can be obtained with high selectivity by reacting a phenol with ammonia in the presence of a cyclohexanone, leading to the completion of the present invention.

The present invention therefore provides a process for the preparation of a diphenylamine represented by the following formula (3):

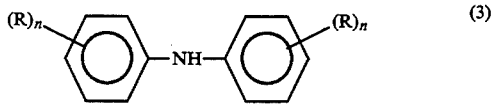

wherein R represents a $C_{8-14}$ alkyl, $C_{5-8}$ cycloalkyl, $C_{8-14}$ alkoxyl, aryl or aryloxyl group and n stands for an integer of 1-5, which comprises reacting, in the presence of a hydrogen transfer catalyst and a cyclohexanone represented by the following formula (1):

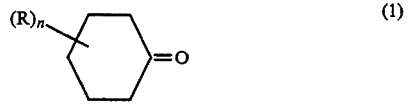

wherein R and n have the same meanings as defined above, ammonia with a phenol represented by the following formula (2):

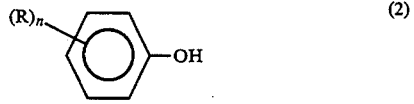

wherein R and n have the same meanings as defined above; and also a process for the preparation of a diphenylamine represented by the formula (3) which comprises converting, in the presence of a hydrogen transfer catalyst under hydrogen pressure, a portion of a phenol represented by the formula (2) to a cyclohexanone represented by the formula (1) and, while using the remaining portion of the phenol (2) as a hydrogen acceptor, thereby forming the cyclohexanone represented by the formula (1) in a reaction system successively, conducting reaction with ammonia.

DETAILED DESCRIPTION OF THE PREFERRED EMBODIMENTS

Examples of R in the formulas (1), (2) and (3) include $C_{8-14}$ alkyl groups, $C_{5-8}$ cycloalkyl groups, $C_{8-14}$ alkoxyl groups, aryl groups such as phenyl and naphthyl, and aryloxyl groups such as phenoxyl and naphthoxyl.

In each of the processes of the present invention, hydrogen formed as a result of dehydrogenation of a cyclohexylimine, said cyclohexylimine having been formed by the reaction between ammonia and the cylohexanone, is used in the same reaction system for the reduction of the phenol, that is, for the formation of the cyclohexanone. Further in the same reaction system, an aniline formed as a result of dehydrogenation of the cyclohexylimine undergoes condensation reaction with the cyclohexanone to form a cyclohexylideneaniline. This cyclohexylideneaniline is then dehydrogenated, whereby a diphenylamine is obtained. The hydrogen formed at this stage is also fully used in the same reaction system for the reduction of the phenol. This process is therefore extremely efficient.

It is preferred to conduct the reaction while charging ammonia in portions or successively to the reaction system without charging it at once. Such a charging manner can suppress by-production of N-(cyclohexyl)anilines, thereby making it possible to conduct the reaction under milder conditions and moreover, to shorten the reaction time.

Taking the preparation of dinonyldiphenylamine, for example, the phenol employed in each of the processes of this invention is prepared by the Friedel-Crafts alkylation between phenol and nonene and is therefore readily available. This reaction to obtain a phenol can be conducted under milder conditions compared with the above-described, conventional Friedel-Crafts alkylation between diphenylamine and nonene and permits preparation of the phenol in a high yield. Each of the processes according to the present invention which employs the phenol is advantageous not only in the yield but also in the fact that owing to the introduction of nonyl groups at the beginning of the reaction, the resulting di-substituted diphenylamine is free of by-products such as the mono-substituted derivative.

Any known hydrogen transfer catalysts can be used in each of the processes of the present invention. Specific examples include Raney nickel, reduced nickel and nickel-bearing catalysts with nickel supported on various carriers such as diatomaceous earth, alumina, pumice, silica gel and acid clay; cobalt catalysts such as Raney cobalt, reduced cobalt, cobalt and cobalt-carrier catalysts; copper catalysts such as Raney copper, reduced copper and copper-carrier catalysts; palladium catalysts such as palladium black, palladium oxide, colloidal palladium, palladium-carbon, palladium-barium sulfate, and palladium-barium carbonate; platinum catalysts such as platinum black, colloidal platinum, platinum sponge, platinum oxide, platinum sulfide and platinum-carrier catalysts such as platinum-carbon; rhodium catalysts such as colloidal rhodium, rhodium-carbon and rhodium oxide; platinum group metal catalysts such as ruthenium catalysts; rhenium catalysts such as rhenium heptaoxide and rhenium-carbon; copper chromium oxide catalysts; molybdenum oxide catalysts; vanadium oxide catalysts; and tungsten oxide catalysts. Among these catalysts, palladium catalysts are preferred, with palladium-carrier catalysts being more preferred and palladium-carbon and palladium-alumina being particularly preferred.

The hydrogen transfer catalyst may be used in an amount of 0.001–1.0 gram atom, preferably 0.002–0.2 gram atom as metallic atoms per gram molecule of ammonia as a raw material.

The phenol usable as another raw material in each of the processes of the present invention is a hydrogen acceptor and as a consequence, it also serves as a source for the cyclohexanone.

Described specifically, the phenol is reduced by the hydrogen formed as a result of dehydrogenation of an intermediate imine, which has been produced by the reaction between ammonia and the cyclohexanone, thereby forming the cyclohexanone. The Schiff base formed by the condensation reaction between the resulting aniline and the cylohexanone is then dehydrogenated so that hydrogen is formed. By this hydrogen, the phenol is similarly reduced to supply the cyclohexanone.

In theory, it is sufficient to use the phenol in an amount of 2.0 equivalents per equivalent of ammonia. It is, however, desired to use the phenol in an amount of at least 2.5 equivalents, preferably 3–7 equivalents per equivalent of ammonia, because use of the phenol in an excess amount, including that serving as a solvent, tends to result in high selectivity to the target product. Amounts smaller than 2.0 equivalents per equivalent of ammonia result in greater by-production of the N-(cyclohexyl)aniline. Amounts outside the above range are therefore not preferred.

When the cyclohexanone is allowed to co-exist in the reaction system from the beginning of the reaction, no particular problem or inconvenience would arise insofar as the cyclohexanone is added in an amount of at least about 0.03 mole per mole of ammonia. The preferred amount of the cyclohexanone can be 0.05–0.50 mole. Amounts smaller than the above lower limit tend to result in a reduced reaction velocity.

When the cylohexanone is not allowed to exist in the reaction system from the beginning of the reaction, on the other hand, it is necessary to hermetically fill a reactor with hydrogen in an amount sufficient to form a suitable amount of the cyclohexanone, that is, at least about 0.06 mole, preferably 0.10–1.00 mole per mole of the ammonia, followed by reaction under heating.

The reaction temperature in each of the processes of the present invention is ordinarily selected from a range of from 150° C. to 300° C., preferably from 180° C. to 230° C. Temperatures lower than 150° C. result in a reduced reaction velocity and greater by-production of the N-(cyclohexyl)aniline. To dehydrogenate the resulting by-product, a higher temperature and moreover, a longer reaction time are needed.

In each of the processes of the present invention, the reaction can advantageously be conducted under pressure. It is desired to conduct the reaction usually within a range of from normal pressure to 5 kg/cm$^2$G, preferably 0.5 kg/cm$^2$G to 3 kg/cm$^2$G.

It is advantageous to conduct the reaction while removing the resulting water. For this purpose, the water can be appropriately removed from the reaction mixture by azeotropic distillation with a solvent such as benzene, toluene or xylene.

After the completion of the reaction, the reaction mixture was allowed to cool down with the pressure lowered to the environmental pressure, followed by filtration for the separation of the catalyst. The catalyst so separated can be used again. The filtrate is, on the other hand, distilled under reduced pressure to remove the remaining phenol including the cyclohexanone, whereby the diphenylamine is obtained as a residue. The phenol so recovered, which contains the cyclohexanone, can be recycled to the reaction system, as is, for reuse.

According to each of the processes of the present invention, a diphenylamine in which both the phenyl groups are substituted can be obtained easily by employing a corresponding phenol and ammonia as described above.

The present invention will hereinafter be described specifically by the following Examples.

EXAMPLE 1

A stainless steel autoclave whose internal capacity was 500 ml was charged with 110.18 g (0.5 mole) of p-nonylphenol, 13.46 g (0.06 mole) of p-nonylcyclohexanone and 1.75 g of 5% Pd/C (product of N.E. Chemcat Corporation). After charging a dropping funnel with a solution of 3.40 g (0.2 mole) of ammonia in 110.18 g (0.5 mole) of p-nonylphenol, the autoclave was purged with nitrogen and heated to 225° C. At the same temperature, the ammonia-nonylphenol solution in the dropping funnel was added dropwise over 4 hours. After completion of the dropwise addition, stirring was continued for further a one hour while the contents are maintained at the same temperature. Water resulting from the reaction was subjected to azeotropic distillation with toluene charged into the autoclave, condensed in a reflux condenser and then separated by a separator. The reaction mixture was then allowed to cool down and then, the 5% Pd/C was filtered off from the reaction mixture. A portion of the filtrate was sampled and analyzed by liquid chromatography. As a result, the yield of dinonyldiphenylamine was found to be 98.9% (based on the ammonia used).

EXAMPLE 2

A stainless steel autoclave whose internal capacity was 500 ml was charged as in Example 1, except for the omission of p-nonylcyclohexanone from the initial charge. The autoclave was purged with nitrogen, followed by pressurization to 5 kg/cm$^2$G with hydrogen. Hydrogen was charged in an amount of about 0.3 mole per mole of ammonia, which was equivalent to the amount of nonylcyclohexanone obtained from the nonylphenyl consumed for the reaction. In a similar manner to Example 1, the materials in the autoclave were heated and reacted. As a result, it was found that the yield of dinonyldiphenylamine was 97.8%.

EXAMPLE 3

A stainless steel autoclave whose internal capacity was 500 me was charged with 220.35 g (1 mole) of nonylphenol, 3.40 g (0.2 mole) of ammonia, 13.46 g (0.06 mole) of p-nonylcyclohexanone and 1.75 g of 5% Pd/C (product of N.E. Chemcat Corporation). The autoclave was purged with nitrogen and then heated to 225° C. At the same temperature, the resulting mixture was allowed to react for 5 hours under stirring. Water resulting from the reaction was subjected to azeotropic distillation with toluene charged into the autoclave, condensed in a reflux condenser and then separated by a separator. The reaction mixture was allowed to cool down and the 5% Pd/C was then filtered off from the reaction mixture. A portion of the filtrate was sampled and analyzed by liquid chromatography. As a result, the yield of dinonyldiphenylamine was found to be 83%.

EXAMPLE 4

A stainless steel autoclave whose internal capacity was 500 ml was charged in a similar manner to Example 3, except for the omission of p-nonylcyclohexanone from the initial charge. The autoclave was purged with nitrogen, followed by pressurization to 5 kg/cm²G with hydrogen. Hydrogen was charged in an amount of about 0.3 mole which was equivalent to the amount of nonylcyclohexanone prepared from 1 mole of the non-ylphenol consumed for the reaction. In a similar manner to Example 3, the materials in the autoclave were heated and reacted. As a result, it was found that the yield of the dinonyldiphenylamine was 79%.

EXAMPLES 5-11

In each Example, a reaction was carried out as in Example 1 except that the phenol shown in Table 1 and its corresponding cyclohexanone were employed instead of p-nonylphenyl and p-nonylcyclohexanone. The results are presented in Table 1.

TABLE 1

| Example | Phenol | Yield (%) |
| --- | --- | --- |
| 5 | -P-octylphenol | 85.2 |
| 6 | P-dodecylphenol | 81.6 |
| 7 | P-phenylphenol | 87.1 |
| 8 | P-phenoxyphenol | 78.5 |
| 9 | P-cyclohexylphenol | 82.6 |
| 10 | 2,4-dinonylphenol | 72.8 |
| 11 | 2,4-dioctylphenol | 74.3 |

What is claimed is:

1. A process for the preparation of a diphenylamine represented by the following formula (3):

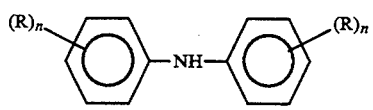

(3)

wherein R represented a $C_{8-14}$ alkyl, $C_{5-8}$ cycloalkyl, and $C_{8-14}$ alkoxyl, aryl or aryloxyl group and n stands for an integer of 1–5, which comprises reacting, in the presence of a hydrogen transfer catalyst, a cyclohexanone represented by the following formula (1):

(1)

wherein R and n have the same meanings as defined above, ammonia, and a phenol represented by the following formula (2):

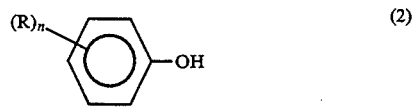

(2)

wherein R an n have the same meanings as defined above in an amount of at least 2.5 moles per mole of ammonia while removing water resulting from the reaction.

2. A process for the preparation of a diphenylamine represented by the following formula (3):

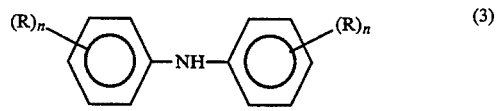

(3)

wherein R represented a $C_{8-14}$ alkyl, $C_{5-8}$ cycloalkyl, $C_{8-14}$ alkoxyl, aryl or aryloxyl group and n stands for an integer of 1–5, which comprises reacting, in the presence of a hydrogen transfer catalyst, ammonia, a phenol represented by the following formula (2):

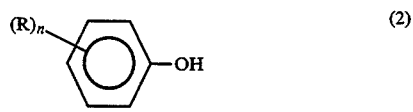

(2)

wherein R and n have the same meanings as defined above in an amount of at least 2.5 moles per mole of ammonia, and a cyclohexanone represented by the following formula (1):

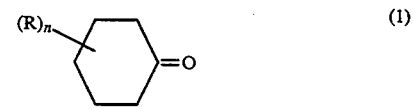

(1)

wherein R and n have the same meanings as defined above, wherein a portion of the phenol is converted under hydrogen pressure to cyclohexanone represented by formula (1) and then the remaining portion of the phenol is reacted with ammonia in the presence of the cyclohexanone and the hydrogen transfer catalyst while removing water resulting from the reaction.

3. A process according to claim 1, wherein the cyclohexanone is used in an amount of 0.03 to 0.50 mole per mole of ammonia.

4. A process according to claim 1, wherein the reaction is conducted at 150° to 300° C.

5. A process according to claim 4, wherein the reaction is conducted under normal pressure to 5 kg/cm²G.

6. A process according to claim 2, wherein 0.06 to 1.00 mole of the hydrogen is used per mole of the phenol.

7. A process according to claim 2, wherein the reaction with ammonia is conducted at 150° to 300° C.

8. A process according to claim 2, wherein the reaction with ammonia is conducted under normal pressure to 5 kg/cm²G.

* * * * *

UNITED STATES PATENT AND TRADEMARK OFFICE
CERTIFICATE OF CORRECTION

PATENT NO. : 5,449,829
DATED : September 12, 1995
INVENTOR(S) : Chiyuki Kusuda et al.

It is certified that error appears in the above-indentified patent and that said Letters Patent is hereby corrected as shown below:

On the title page, item [73] Assignee:, delete "Mitsuit" and insert therefor --Mitsui--.

IN THE CLAIMS:

Claim 5, line 56, delete "4" and insert therefor --1--.

Signed and Sealed this

Sixteenth Day of July, 1996

Attest:

BRUCE LEHMAN

Attesting Officer

Commissioner of Patents and Trademarks